United States Patent [19]

Miller et al.

[11] 4,357,334

[45] Nov. 2, 1982

[54] USE OF VLB 3-(2-CHLOROETHYL) CARBOXAMIDE IN TREATING NEOPLASMS

[75] Inventors: Jean C. Miller; Gerald E. Gutowski, both of Indianapolis, Ind.

[73] Assignee: Eli Lilly and Company, Indianapolis, Ind.

[21] Appl. No.: 132,246

[22] Filed: Mar. 20, 1980

[51] Int. Cl.³ .................. A61K 31/475; C07D 519/04
[52] U.S. Cl. ................................ 424/262; 260/244.4
[58] Field of Search ...................... 260/244.4; 424/262

[56] References Cited

U.S. PATENT DOCUMENTS

| | | | |
|---|---|---|---|
| Re. 30,561 | 3/1981 | Miller et al. | 260/244.4 |
| 4,096,148 | 6/1978 | Miller et al. | 260/244.4 |
| 4,160,767 | 7/1979 | Miller et al. | 260/244.4 |
| 4,203,898 | 5/1980 | Cullinan et al. | 260/244.4 |

FOREIGN PATENT DOCUMENTS

| | | |
|---|---|---|
| 858451 | 8/1978 | Belgium . |
| 2415980 | 10/1974 | Fed. Rep. of Germany . |
| 2739443 | 3/1978 | Fed. Rep. of Germany . |
| 1538921 | 1/1979 | United Kingdom . |

OTHER PUBLICATIONS

Conrad, et al., J. Med. Chem., vol. 22, No. 4, pp. 391–400 (1979).
Barnett, et al., J. Med. Chem., 21, (1), pp. 88–96 (1978).

*Primary Examiner*—Donald G. Daus
*Assistant Examiner*—Diana G. Rivers
*Attorney, Agent, or Firm*—James L. Rowe

[57] ABSTRACT

VLB 3-(2-chloroethyl)carboxamide, the corresponding 4-desacetyl derivative and salts thereof, useful in treatment of neoplasms in pharmaceutical dosage forms.

5 Claims, No Drawings

USE OF VLB 3-(2-CHLOROETHYL) CARBOXAMIDE IN TREATING NEOPLASMS

BACKGROUND OF THE INVENTION

The alkaloids obtainable from *Vinca rosea* represent one of the most productive areas of chemistry for drugs which adversely affect the growth of experimental malignancies in mammals. Initially, only some of the alkaloids obtainable from the leaves of the plant by extraction and purifiable by chromatography were found to be active. These active anti-neoplastic vinca alkaloids obtained directly from the plant have been found to be dimeric indole-dihydroindole alkaloids representable by the formula:

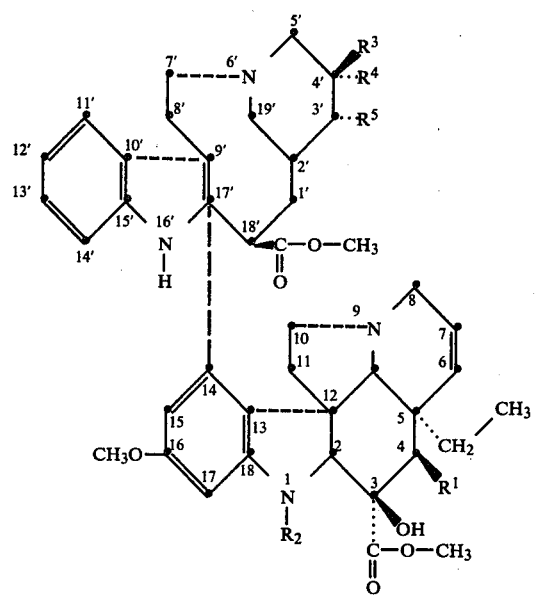

In the above formula where $R^1$ is acetoxy, $R^2$ is methyl, $R^3$ is hydroxyl, $R^4$ is ethyl and $R^5$ is H, VLB (vincaleucoblastine, vinblastine) is represented; where $R^1$ is acetoxy, $R^2$ is formyl, $R^3$ is hydroxyl, $R^4$ is ethyl and $R^5$ is H, vincristine is represented; where $R^1$ is acetoxy, $R^2$ is methyl, $R^3$ is ethyl, $R^4$ is hydroxyl, and $R^5$ is H, leurosidine is represented; where $R^1$ is acetoxy, $R^2$ is methyl or formyl, $R^3$ is ethyl and $R^4$ and $R^5$ taken together form an α-epoxide ring, leurosine and leuroformine, respectively are represented. Literature references to the above alkaloids are as follows: leurosine (U.S. Pat. No. 3,370,057), VLB (U.S. Pat. No. 3,097,137), leuroformine (Belgian Pat. No. 811,110); leurosidine (vinrosidine) and leurocristine (to be referred to hereafter as vincristine) (both in U.S. Pat. No. 3,205,220).

Two of the above alkaloids, VLB and vincristine, are now marketed for the treatment of malignancies, particularly the leukemias and related diseases, in humans. The two marketed alkaloids are customarily administered by the i.v. route. Two others, leurosidine and leuroformine, have been on clinical trial in the U.S. or in Europe.

Chemical modification of the Vinca alkaloids started slowly for several reasons. In the first place, the molecular structures involved are extremely complex, and chemical reactions which modify one specific functional group of the molecule without affecting other groups have been difficult to develop. Secondly, dimeric alkaloids lacking desirable chemotherapeutic properties have been recovered or produced from *Vinca rosea* extracts, and a determination of their structures has led to the conclusion that these inactive compounds are closely related structurally to, and even isomeric with, the active alkaloids.

One of the more recent, and more successful, modifications of the basic indole-dihydroindole structure has been the preparation of C-3 carboxamide and carboxhydrazide derivatives. Many of these are active anti-tumor agents (see U.S. Pat. No. 4,166,810, and Conrad et al. *J. Med. Chem.*, 22, 391 (1979). These compounds are extremely interesting because, for example, the 3-carboxamides of VLB are more active against Ridgeway osteogenic sarcoma and Gardner lymphosarcoma than is VLB, the basic alkaloid from which they are derived. Certain of these amide derivatives approach the activity of vincristine against these two tumors. In particular, 4-desacetyl VLB C-3 carboxamide (vindesine) currently on clinical trial in humans, appears to have less neurotoxicity than does vincristine and to be effective against some of leukemias including those which are vincristine-resistant.

Other amides of VLB and 4-desacetyl VLB which have been described in the literature include the N-ethylamide, the N-(2-hydroxy)ethylamide, the N-(2-methoxy)ethyl amide, the corresponding thio compounds, and the N-n-propylamide.

While VLB and a few other antineoplastic dimeric vinca alkaloids are active when administered by the oral route, far higher doses are required than when utilizing the more conventional intravenous route. Of all the VLB derivatives tested to date, only the oxazolidinedione derivatives of U.S. Pat. Nos. 4,096,148 and 4,160,767 have oral activity at a dosage range approaching that of the i.v. dose. The oral dose levels of these oxazolidinedione derivatives of VLB etc. are higher than the i.v. dose levels for vincristine.

It is an object of this invention to provide a vinca dimer having oral activity and an anti-tumor spectrum approaching the i.v. activity and spectrum of vincristine.

SUMMARY OF THE INVENTION

In fulfillment of the above and other objects, this invention provides compounds of the formula:

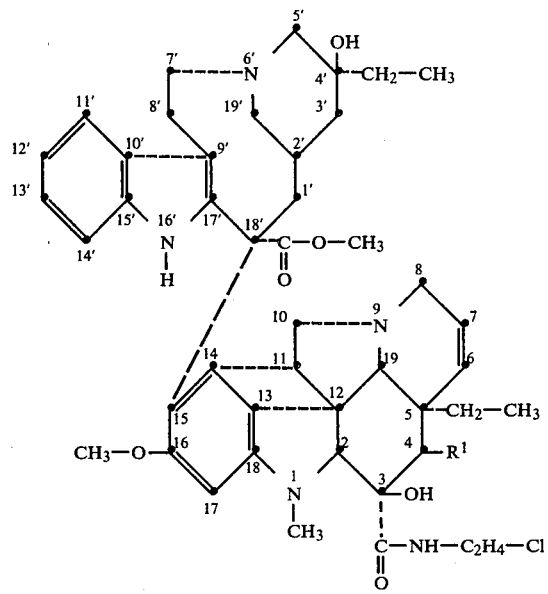

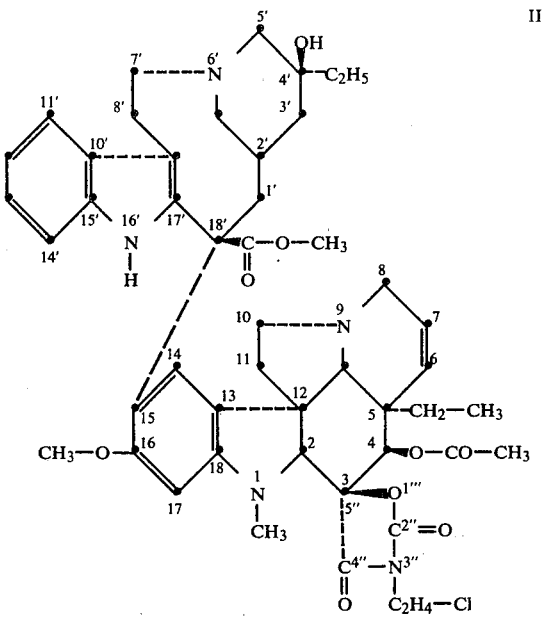

wherein R¹ is OH or acetoxy

When R¹ is acetoxy, the compound is named VLB 3-(2-chloroethyl)carboxamide and when R¹ is OH, the compound is named 4-desacetyl VLB 3-(2-chloroethyl)-carboxamide. The above free bases are customarily utilized therapeutically in the form of an acid addition salt formed with a non-toxic acid, preferably sulfuric acid. Useful non-toxic acids include inorganic acids such as: hydrochloric acid, nitric acid, phosphoric acid, sulfuric acid, hydrobromic acid, hydriodic acid, phosphorus acid and the like, as well as salts of nontoxic organic acids including aliphatic mono and dicarboxylates, phenyl-substituted alkanoates, hydroxy alkanoates and alkandioates, aromatic acids, aliphatic and aromatic sulfonic acids, etc. Such pharmaceutically-acceptable salts thus include the sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptaonate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

VLB 3-(2-chloroethyl)carboxamide of this invention can be prepared from the corresponding oxazolidinedione of U.S. Pat. No. 4,096,148, Example 4. This latter compound has the following structure.

and is named VLB 3''-(2-chloroethyl)-3-spiro-5''-oxazolidine-2'',4''-dione. Treatment of the corresponding sulfate salt with water or with dilute acid or base yields VLB 3-(2-chloroethyl)carboxamide, one of the compounds of this invention. Reaction of this latter compound with dilute base yields the corresponding 4-desacetyl derivative, another compound of this invention. Thus, reaction of the oxazolidinedione with dilute base can yield, depending on temperature, reaction time and pH, VLB 3-(2-chloroethyl)carboxamide and the C-4 deacetyl derivative. The carboxamide product is separated from the starting oxazolidinedione by HPLC or other chromatographic procedure. VLB 3-(2-chloroethyl)carboxamide is best characterized physically by $^{13}C$ nmr. The following example illustrates the preparation of the latter compound by treatment of the oxazolidinedione sulfate salt with water.

EXAMPLE 1

A solution of 1.3647 g. of VLB 3'''-(2-chloroethyl)-3-spiro-5''-oxazolidine-2'',4''-dione sulfate was prepared in about 30 ml. of water: pH=2.5. The solution was stirred at ambient temperature for about two weeks and then at about 50° C. for 24 hours. The solution was then made basic by the addition of 14 N aqueous ammonium hydroxide. The resulting alkaline solution was extracted four times with an equal volume of methylenedichloride. The methylenedichloride extracts were combined and the solvent evaporated therefrom in vacuo. The resulting residue was chromatographed over silica gel. Fractions containing VLB-3-(2-chloroethyl)carboxamide were combined and the solvent removed by evaporation in vacuo. A yield of 58 mg. of pure VLB 3-(2-chloroethyl)carboxamide were obtained. The compound had the following physical characteristics:

Infrared spectrum ($CHCl_3$) peaks at 3690, 3600, 1735, 1720, 1680, 1615 and 1500 cm$^{-1}$.

pKa (66% DMF) 4.7; 7.4 nmr (360 MHz, $CDCl_3$)δ at 0.83, 0.92, 1.33, 2.08, 2.80, 2.83, 3.64, 3.67, 3.80, 3.98, 5.32, 5.56, 5.86, 6.1, 6.62, 7.14, 7.5, 8.06, 10.08.

| $^{13}C$ nmr | | | |
|---|---|---|---|
| Vindoline Portion | | Catharanthine Portion | |
| carbon # | ppm | carbon # | ppm |
| 2 | 84.7 | 2 | 131.6 |
| 3 | 50.4 | 3 | 48.2 |
| 5 | 50.4 | 5 | 55.8 |
| 6 | 45.1 | 6 | 28.8 |
| 7 | 53.4 | 7 | 117.0 |
| 8 | 122.5 | 8 | 129.6 |
| 9 | 123.4 | 9 | 118.5 |
| 10 | 120.5 | 10 | 122.1 |
| 11 | 158.2 | 11 | 118.8 |
| 12 | 94.8 | 12 | 110.5 |
| 13 | 152.9 | 13 | 135.0 |
| 14 | 124.4 | 14 | 30.2 |
| 15 | 130.3 | 15 | 41.2 |
| 16 | 79.6 | 16 | 55.7 |
| 17 | 76.5 | 17 | 34.4[d] |
| 18 | 8.4 | 18 | 6.9 |
| 19 | 30.8 | 19 | 34.6[d] |
| 20 | 42.5 | 20 | 69.6 |
| 21 | 65.9 | 21 | 64.4 |
| COOR | 170.5 | COOR | 175.0 |
| AroCH3 | 55.8 | COOMe | 52.3 |
| NCH3 | 38.6 | | |
| ACME | 21.0 | | |
| COOMe | — | | |
| AcCO | 172.4 | | |
| O=C(-O-)(-N(-CH2-CH2-Cl)) | 43.3, 41.7 | | |

[d] assignments may be exchanged

Other similar hydrolyses were carried out with the following results: Stirring for 12 days at pH=4.2 gave 9% conversion of the oxazolidinedione to the 2-chloroethylcarboxamide. Stirring for three days at ambient temperature at pH=7 gave a 6% conversion and at pH 2 a 16% conversion.

A more rapid method of preparing the compounds of this invention utilizes an amide-azide synthesis from Conrad et al. (loc. cit.). As outlined therein, the procedure consists of first reacting VLB with hydrazine hydrate to yield a 4-desacetyl VLB 3-carboxhydrazide, the hydrazine hydrate being sufficiently basic to hydrolyze the 4-acetoxy group. The hydrazide is then converted to the corresponding azide by the action of nitrous acid or nitrite ion. The thus formed azide then reacts with primary or secondary amines to yield a 3-carboxamide. It was not expected that the hydrazide-azide reaction would be operative to prepare a 2-chloroethylamide since the intermediate primary amine which must react with the azide function is a 2-chloroethylamine. Such amines can internally cyclize to form aziridines, and the aziridine ring can open to yield in aqueous solution the corresponding 2-hydroxyethylamine or 2-hydroxyethylamide as the case may be. Nevertheless, reaction of 4-desacetyl VLB 3-carboxazide with 2-chloroethylamine yields 4-desacetyl VLB 3-(2-chloroethyl)carboxamide in satisfactory yield as will be seen from the following example.

EXAMPLE 2

A solution of 531 mg. of 4-desacetyl VLB 3-carboxazide was prepared following the method of Conrad et al. Method A (loc. cit.) in 5 ml. of THF. To this solution was added an excess of 2-chloroethylamine hydrochloride and 7 ml. of triethylamine. About 5–10 ml. of methylenedichloride were added to dissolve the azide. The reaction mixture was stirred for about 72 hours at ambient temperature in the dark at which time TLC of an aliquot showed no spot corresponding to starting material. 200 ml. of water were added. The aqueous mixture was then extracted four times with 200 ml. of portions of methylenedichloride. The methylenedichloride extracts were combined and the combined extracts washed twice with saturated aqueous sodium bicarbonate. The methylenedichloride solution was then dried and the methylenedichloride removed in vacuo. A residue was obtained comprising 4-desacetyl VLB 3-(2-chloroethyl)carboxamide weighing 458.1 mg. and having the following physical characteristics;

Mass spectrum: peaks at 815 and 779.

Infrared spectrum (chloroform): peaks at 3550, 3470, 3400, 1730, 1665, 1615 and 740 cm$^{-1}$.

nmr (CDCl$_3$): 0.87, 0.92, 2.79, 3.41, 3.57, 3.63, 3.72, 3.75, 4.15, 5.75, 6.03, 6.55, 7–8, 798, 9.6 ppm.

A third method of synthesis of the compounds of this invention involves the reaction of 4-desacetyl VLB 3-(2-hydroxyethyl)carboxamide (from Conrad et al. loc. cit.) with triphenylphosphine and carbon tetrachloride [see Downie et al., Chem. Ind., 900 (1966) or Weiss and Snyder, J. Org. Chem., 36, 404 (1971)]. By this procedure, the hydroxy group is replaced by a chlorine with the concomitant production of triphenylphosphine oxide. This procedure is further illustrated in Example 3.

EXAMPLE 3

A solution was prepared containing 91.9 mg. of 4-desacetyl VLB-3-(2-hydroxyethyl)carboxamide in 2 ml. of methylenedichloride and 6 ml. of carbon tetrachloride. An excess of triphenylphosphine (69.6 mg.) was added and the resulting mixture stirred at ambient temperature. After several hours, a precipitate had deposited on the sides of the flask, therefore an additional 4 ml. of methylenedichloride were added to solubilize this precipitate. After stirring for 24 hours, TLC indicated that the reaction was essentially complete. 20 ml. of 1 N aqueous hydrochloric acid were added and the resulting acidic mixture extracted with three 20 ml. portions of methylenedichloride. The acidic layer was then made basic by the addition of 14 N aqueous ammonium hydroxide and the resulting alkaline layer extracted four times with 20 ml. portions of methylenedichloride. These latter methylenedichloride extracts were combined and dried. Evaporation of the solvent yielded 81.0 mg. of 4-desacetyl VLB 3-(2-chloroethyl)carboxamide. Acetylation of this compound using excess acidic anhydride in methylenedichloride and stirring the resulting mixture for 27 hours at ambient temperature yields VLB 3-(2-chloroethyl)carboxamide of Example 1.

VLB 3-(2-chloroethyl)carboxamide is an antimitotic compound which adversely affects the growth of malignant cells.

This activity was manifested in a standard mitotic inhibition test employing Chinese hamster ovary cells VLB C-3 N-(2-chloroethylcarboxamide had a mitotic index+(15–25% inhibition) at $2.0 \times 10^{-2}$ mcg/ml. (same as that for VLB).

The bases of this invention and their salts preparable by the processes disclosed herein are active also in vivo against transplanted tumors in mice. To demonstrate such activity, a protocol was used involving the administration of the drug by the intraperitoneal or oral route, at selected dose levels, against GLS (Gardner lymphosarcoma), $B_{16}$ melanoma, 755 adenocarcinoma and $C_3H$ mammary carcinoma.

The following table—Table 1—gives the results of this demonstration in which mice bearing the transplanted tumor were treated with a compound of this invention. In the table, column 1 gives the name of the compound; column 2, the dosage given and column 3, the percent inhibition of tumor growth (I) or prolongation of life (PL). The following dosage regimens were employed: every day for 7 or 10 days after inoculation; and every fourth day (three doses) starting at the third day after inoculation.

TABLE 1

| Name of Compound | Tumor | Dosage (mg/kg) regimen | Route | Percent Inhibition (I) or Prolongation (PL) |
|---|---|---|---|---|
| VLB 3-(2-chloroethyl)-carboxamide sulfate | B16 | 2 × 3 | PO | 43 PL |
| | | 3 × 3 | PO | 42 (1)* PL |
| | | 4 × 3 | PO | 77, Toxic PL |
| | | 5 × 3 | PO | Toxic |
| | | .5 × 3 | IP | 94, (4) PL |
| | | .6 × 3 | IP | 64, (2) PL |
| | | .7 × 3 | IP | 50 (1) PL |
| | | .8 × 3 | IP | 80 (1) PL |
| | C₃H | .8 × 3 | IP | 94 I |
| | | .7 × 3 | IP | 86 I |
| | | .65 × 3 | IP | 77 I |
| | | .55 | IP | 64 |
| VLB 3-(2-chloroethyl)-carboxamide sulfate | C₃H | 3 × 3 | PO | Toxic |
| | | 2.5 × 3 | PO | 92 I |
| | | 2 × 3 | PO | 58 I |
| | | 1.5 × 3 | PO | 49 I |
| | 755 | 1-1.5 × 3 | IP | Toxic |
| | | 0.75 × 3 | IP | 76 I |
| | | 0.5 × 3 | IP | 26 I |
| | | 7.5 × 3 | PO | Toxic |
| | | 5 × 3 | PO | 95 I |
| | | 3 × 3 | PO | 81 I |
| | G.L.S. | 2 × 10 | PO | Toxic |
| | | 1 × 10 | PO | 83 I |

*parentheses enclose no. of indefinite survivors

In utilizing the novel compounds of this invention as anti-tumor agents in mammals, either the parenteral or oral route of administration may be employed. The drug is customarily mixed with a pharmaceutically suitable carrier. With parenteral administration, the intravenous route is preferred although, with smaller mammals such as mice, the intraperitoneal route may be used. For intravenous administration, isotonic solutions containing 1-10 mg./ml. of a salt of an alkaloidal base of formula II above are employed. The drug is administered at a dose of from 0.01 to 10 mg./kg. and preferably from 0.05 to 1 mg./kg. of mammalian body weight once or twice a week or every two weeks depending on both the activity and the toxicity of the drug. An alternative method of arriving at a therapeutic dose is based on body surface area with a dose in the range 0.1 to 10 mg./meter squared of mammalian body surface administered every 7 or 17 days or thrice weekly. For oral administration, a suitable quantity of a pharmaceutically-acceptable salt formed with a non-toxic acid, preferably a sulfate salt, is mixed with starch or other inert pharmaceutically-acceptable excipient and the mixture placed in telescoping gelatin capsules each containing from 7.5-50 mg. of active ingredients. Similarly, the anti-neoplastically active salt can be mixed with starch, a binder, and a lubricant and the mixture compressed into tablets each containing from 7.5-50 mgs. of salt. The tablets may be scored if lower or divided dosages are to be used. In i.v. administration isotonic solutions are employed containing 1-10 mg./ml. of a non-toxic salt and the drug is administered at the rate of from 0.01 to 1 mg./kg. and preferably from 0.1 to 1 mg./kg. of mammalian body weight once or twice a week or every two weeks. The oral dose is from 2 to 10 times the i.v. dose, with the lower dosage levels being effective against a majority of tumors.

As would be expected, the compounds of this invention differ in their anti-tumor spectrum from that of VLB, leurocristine and vindesine in the same way that the anti-tumor spectra of those compounds differ among themselves, one drug being more effective against certain tumors or classes of tumors and less effective against others. However, in utilizing the (2-chloroethyl carboxamides of this invention clinically, an oncologist would administer one of them initially by the same route in the same vehicle and against the same types of tumors as employed clinically with vindesine, leurocristine and VLB. Differences in dosage level would, of course, be based on relative oncolytic potency and toxicity.

The high degree of oral activity of VLB 3-(2-chloroethyl)carboxamide and its 4-desacetyl derivative makes them particularly desirable oncolytic agents for use in humans and suitable candidates for a clinical trial. Such clinical trials are generally carried out in accordance with a procedure suggested by S. K. Carter in a section headed "Study Design Principles for the Clinical Evaluation of New Drugs as Developed by the Chemotherapy Programme of the National Cancer Institute" to be found on pages 242-289 of a recent book "The Design of Clinical Trials in Cancer Therapy" edited by Maurice Staquet (Futura Publishing Co., New York, 1973). The above section refers to 10 "signal" tumors which have been designated by the National Cancer Institute as those tumors against which clinical trial candidates should be screened. These include adenocarcinoma of the breast, adenocarcinoma of the colon, bronchogenic carcinoma, adenocarcinoma of the pancreas, ovarian cancer, malignant melonoma, acute myelocytic leukemia, acute lymphocytic leukemia, lymphomatous disease and malignant glyoma. VLB 3-(2-chloroethyl)carboxamide would be tested clinically by the oral route against these tumors as well as other tumors known to be susceptible to i.v. administration of vincristine, VLB or vindesine. After its potency, nature and degree of side effects etc. had been established, the drug would be tried against tumors for which there is no therapy. After preliminary tests were concluded and the results published, the drug would be used against tumors susceptible to its action at relatively non-toxic dose levels.

We claim:

1. The method of treating neoplasms which comprises administering to a mammal suffering from a vindesine-susceptible neoplasm selected from the group consisting of melanoma, adenocarcinoma, mammary carcinoma, lymphosarcoma, osteogenic sarcoma and leukemia, an antineoplastically-effective amount of a compound of the formula:

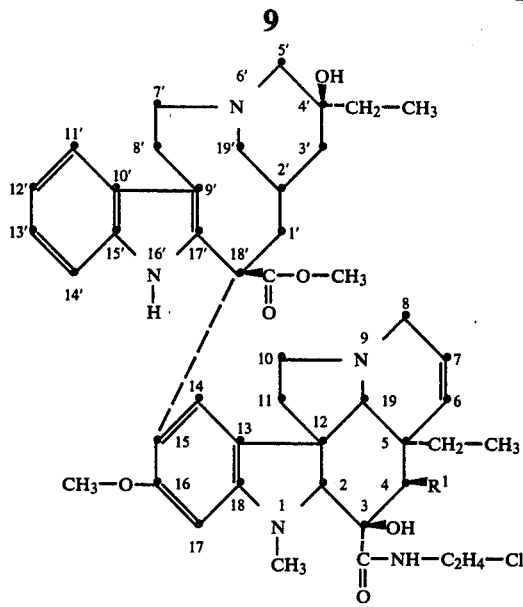

wherein R[1] is OH or acetoxy and pharmaceutically-acceptable acid addition salt thereof.

2. A method according to claim 1 in which VLB 3-(2-chloroethyl)carboxamide sulfate is used.

3. A method according to claim 2 in which the drug is administered orally at a dose level in the range 0.2–10 mg./kg. of mammalian body weight.

4. A method according to claim 1 in which 4-desacetyl VLB 3-(2-chloroethyl)carboxamide is used.

5. A method according to claim 2 in which the drug is administered parenterally at a dose level in the range 0.1 to 10 mg./meter squared of mammalian body surface.

* * * * *